US00PP27952P3

(12) United States Plant Patent
Lewis

(10) Patent No.: US PP27,952 P3
(45) Date of Patent: May 2, 2017

(54) ***PRUNUS* ROOTSTOCK NAMED 'SAM 1'**

(50) Latin Name: *Prunus dulcis*
Varietal Denomination: Sam 1

(71) Applicant: Pamela Samantha Lewis, Chico, CA (US)

(72) Inventor: Pamela Samantha Lewis, Chico, CA (US)

(73) Assignee: Pamela Samantha Lewis, Chico, CA (US)

( * ) Notice: Subject to any disclaimer, the term of this patent is extended or adjusted under 35 U.S.C. 154(b) by 14 days.

(21) Appl. No.: 14/544,896

(22) Filed: Mar. 4, 2015

(65) Prior Publication Data

US 2016/0270275 P1 Sep. 15, 2016

(51) Int. Cl.
*A01H 5/00* (2006.01)

(52) U.S. Cl.
USPC ..... Plt./155

(58) Field of Classification Search
USPC ..... Plt./155, 180
See application file for complete search history.

(56) References Cited

PUBLICATIONS

Reighard, Gregory. (Jan. 16, 2013). New Peach (Plum & Apricot) and Apple Rootstocks for the Grower. Presented at the Western Colorado Horticultural Society 70$^{th}$ Annual Convention. Talk retrieved from the Western Colorado Horticultural Society website http://coloradofruit.org/pastprog.html. 13 pages.*

* cited by examiner

*Primary Examiner* — Susan McCormick Ewoldt
*Assistant Examiner* — Karen Redden
(74) *Attorney, Agent, or Firm* — Randall Danskin P.S.

(57) ABSTRACT

A new and distinct variety of root stocks is described and which is characterized as to novelty by its resistance to Oak Root fungus and Root-Knot nematodes.

5 Drawing Sheets

Latin name: *Prunus dulcis*.
Varietal denomination: 'SAM 1'.

BACKGROUND OF THE VARIETY

The present invention relates to a new and distinct variety of *Prunus* rootstock, *Prunus dulcis*, and which has been denominated varietally hereinafter as 'SAM 1.'

ORIGIN

The new variety of rootstock was discovered in 2005 within the commercial orchard of the inventor and which is located near Durham, Butte County, Calif. Local real estate records show that this orchard was planted in the early 1930s. Historical records indicate that from the late 1800s to the early 1950s, almonds produced in the State of California were typically grown on almond seedlings. Sources of these almond seedlings were typically derived from local wild trees of the bitter almond and/or hard-shelled almond seedling varieties. Many of these early-day almond rooted orchards were grown, "dryland," that is, without supplemental irrigation. In the late 1940s and early 1950s, and as supplemental irrigation of almond orchards became more prevalent in the State of California, the use of peach seedlings for rootstocks of almond trees became more widespread. Those skilled in the art recognize that peach roots are generally more resistant to wet soil condition than almond tree roots. The 'Lovell' rootstock (unpatented) became the most resistant of all peach root stock adopted by growers.

Currently, and based upon the inventor's best knowledge, almost no new commercial orchards in the State of California are planted on almond seedling rootstock.

The original orchard of discovery, and in which the new tree was found, had been replanted in a piecemeal fashion since 1974. This replanting of the orchard of discovery was due to the ongoing death of many trees from both Oak Root fungus ('*Armillaria mella*'); and Crown and Root rot (*Phytophthora* Spp.) and which are sometimes associated with excess water or uneven irrigation practices. Still further, many trees in the original orchard of discovery were previously damaged by high winds.

The Oak Root fungus disease, which is a common, and usually fatal disease in northern California orchards, was found widespread in the orchard of discovery, but appeared to not attack the new variety of rootstock during the more than 75 years that the tree has been growing in the orchard. As trees in the original orchard declined or died, they were replanted on 'Mariana 2624' rootstock (unpatented), and which has demonstrated a good resistance to Oak Root fungus. Further, during the 75 years or more that the current newly discovered tree has been growing in the aforementioned commercial orchard, the newly discovered tree was never damaged by multiple relatively high-impact windstorms that periodically occur in the Butte County region of Northern California. At the time of discovery, the newly discovered tree was producing 'Nonpareil' almonds (unpatented), and which is the most widely planted almond variety among all the almond varieties growing in the State of California.

The 'Nonpareil' almond tree produces a crop which has high quality meat, high production volumes, and is further easy to process. It is a highly preferred variety for grower plantings. The 'Nonpareil,' however, has more graft incompatibility problems than other almond varieties, and is not compatible on the 'Mariana 2624' rootstock (unpatented) and which is sometimes used for almond plantings. The positive performance of the newly discovered 'SAM 1' tree, and the subsequently described performance of the asexually reproduced trees produced by the inventor confirm the compatibility of the new variety 'Sam 1' and which is capable of growing the 'Nonpareil' variety of almond.

As noted earlier, the Oak Root fungus disease is endemic in the State of California and has killed almond trees on a regular basis in the orchard of discovery. The long-term healthy condition of the original newly discovered tree at this orchard of origin would seem to indicate to the inventor that a substantial degree of resistance or tolerance to this disease has been developed by this newly discovered tree. Still further, new test plantings of asexually reproduced and rooted 'Sam 1' trees at the original orchard of discovery, and which have been growing now for more than five (5) years, has shown no newly planted trees being infected by Oak Root fungus.

Those skilled in the art have long recognized that almond rootstock, and peach rootstock, which have been utilized in more recent years for almond trees, are susceptible to Root-Knot nematodes that invade the root tissue and cause substantial damage. This root damage usually causes poor tree and root vigor, and poor tree canopy development. In combination, this results in lowered production of crop. Root-Knot nematodes are present in many soil types throughout California, and are often more severe in lighter soils. Tests conducted in Parlier, Calif., have indicated that the new, and novel variety of root stock has a high degree of tolerance/resistance to Root-Knot nematode.

In addition to the foregoing, the present, newly discovered variety of rootstock appears to have a noteworthy root structure, and which allows or permits the present variety of rootstock to withstand high wind loads, thus preventing wind-related damage to the tree.

As earlier noted, since the widespread adoption of peach seedlings as rootstock (post 1945), the rate of damage to orchards due to high-winds has significantly increased. The damage due to high-winds in orchards is speculated to have come about as a result of the use of peach rootstock inasmuch as peach roots tend to be smaller in size, and are more shallowly rooted in view of current irrigation practices. Consequently, when orchards are exposed to high winds, many trees are often blown down, or damaged beyond recovery. The ability of the recently discovered tree to withstand high wind speeds, even as an old and high stature tree in recent windstorms where winds topped more than 80 miles per hour, is a testimony to the newly discovered rootstock's strength and durability. The attached drawings (FIG. 5) shows a photograph of recently removed trees from the orchard of origin and which shows the root characteristics of the new rootstock, and which demonstrates that most of the side roots extend out and in a downward position. This appears conducive to an eventual deeper rooting than what might be expected from the use of peach rootstock.

The parents of the present newly discovered variety are unknown. A recent DNA analysis suggests that the new variety has a DNA profile most consistent with a hybrid *Prunus* rootstock. However, there are no other records available from the original orchard of origin which would confirm the origin of the newly discovered tree.

On the date of discovery, in 2005, there were only five large, healthy almond trees remaining from the original 1930 era orchard, including the newly discovered tree. The unique size, productivity and survival of these five large, long-lived trees prompted the inventor, following several additional years of observations, and in the fall of 2009, to have cuttings removed from root suckers of two (2) of the five old remaining trees. The cuttings removed from the tree of discovery rooted reasonably well. Other cuttings did not fair so well and were subsequently eliminated from the evaluation. In the spring of 2010, at the instructions of the inventor, small trees of the originally discovered tree were propagated by budding to almond top stock, including three of the more popular almond varieties grown in the State of California, those being, the 'Nonpareil' (unpatented) 'Price' (U.S. Plant Pat. No. 2,350) and 'Monterey' almond varieties (unpatented). These asexually reproduced trees were placed in a test planting in the orchard discovery. Subsequent evaluations of these newly asexually reproduced trees confirmed that they appear identical to the originally discovered tree.

SUMMARY OF THE NEW VARIETY

'Sam 1' is a new and distinct variety of rootstock which appears to be quite useful for growing almonds and other fruit varieties. The present variety also appears novel in view of its demonstrated resistance to Root-Knot nematode, and Oak Root fungus (*Armillaria mellea*). Still further the present new variety is compatible with 'Nonpareil' top stock and further has a root structure which anchors the trees particularly well such that resulting older trees resist damage which may be occasioned by high-winds.

BRIEF DESCRIPTION OF THE DRAWINGS

The accompanying drawings are color photographs of the present variety.

NOT A COMMERCIAL WARRANTY

The following detailed description has been prepared to solely comply with the provisions of 35 USC §112, and does not constitute a commercial warranty, [either expressed or implied] that the present variety will, in the future, display all the botanical, pomological or other characteristics as set forth, hereinafter. Therefore, this disclosure may not be relied upon to support any future legal claims including, but not limited to, breach of warranty of merchantability or fitness for any particular purpose, or non-infringement which is directed, in whole, or in part, to the present variety.

DETAILED DESCRIPTION

Referring more specifically to the pomological and botanical details of this new and distinct variety of rootstock, the following has been observed during the 2014 growing season under the ecological conditions prevailing in an orchard which is located near Durham, Butte County, Calif. All major color code designations are by reference to The Royal Horticultural Society Colour Chart, 3rd Ed., provided by The Royal Horticultural Society of Great Britain.

TREE

Tree vigor: Considered vigorous for the species.

Figure 1:
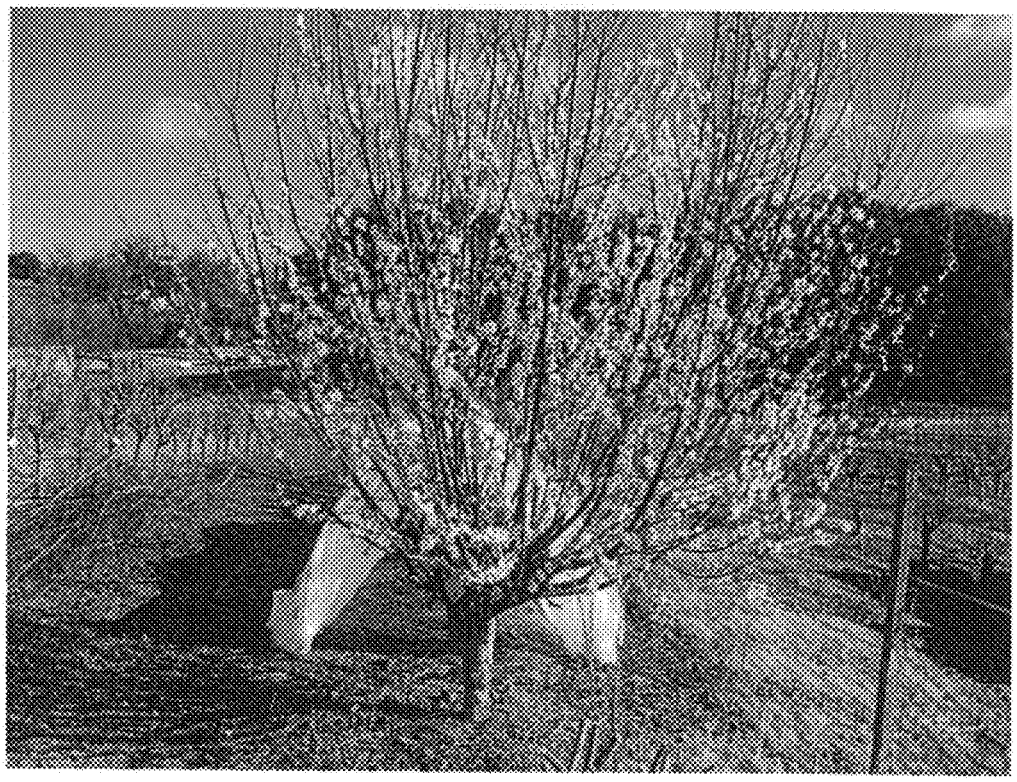
FIG. 1 depicts a second generation tree of the present variety in full bloom at the orchard discovery.
Figure 2:
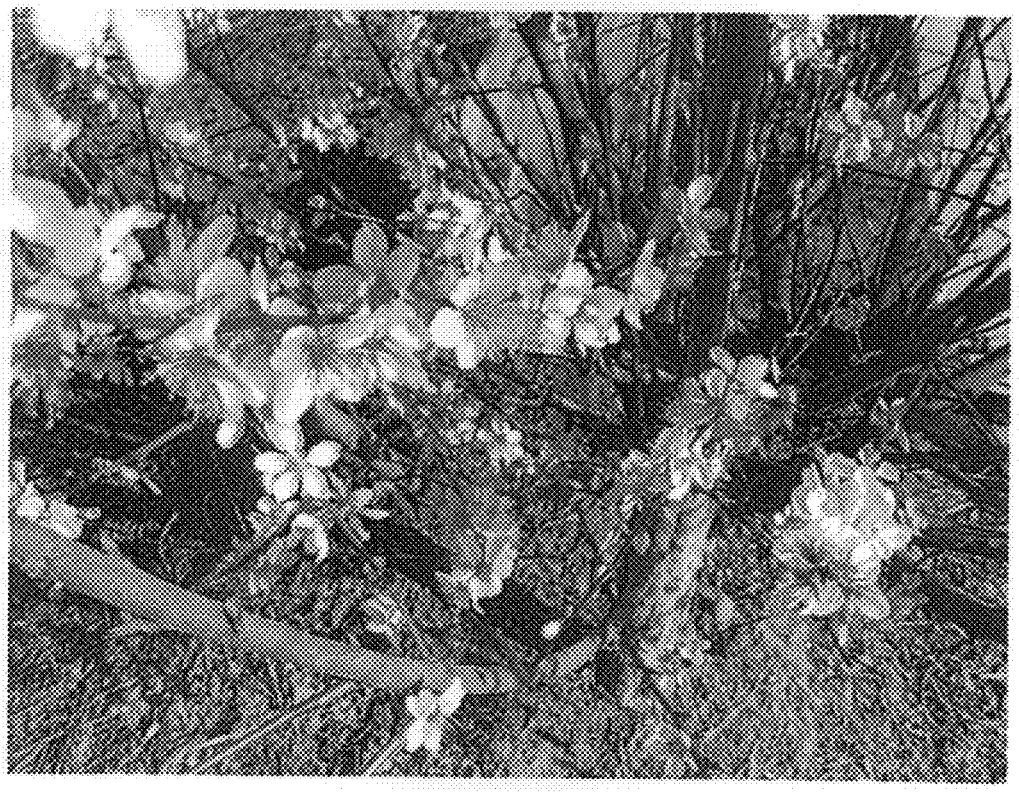
FIG. 2 depicts the blossom characteristics of a second generation tree of the present variety.
Figure 3:
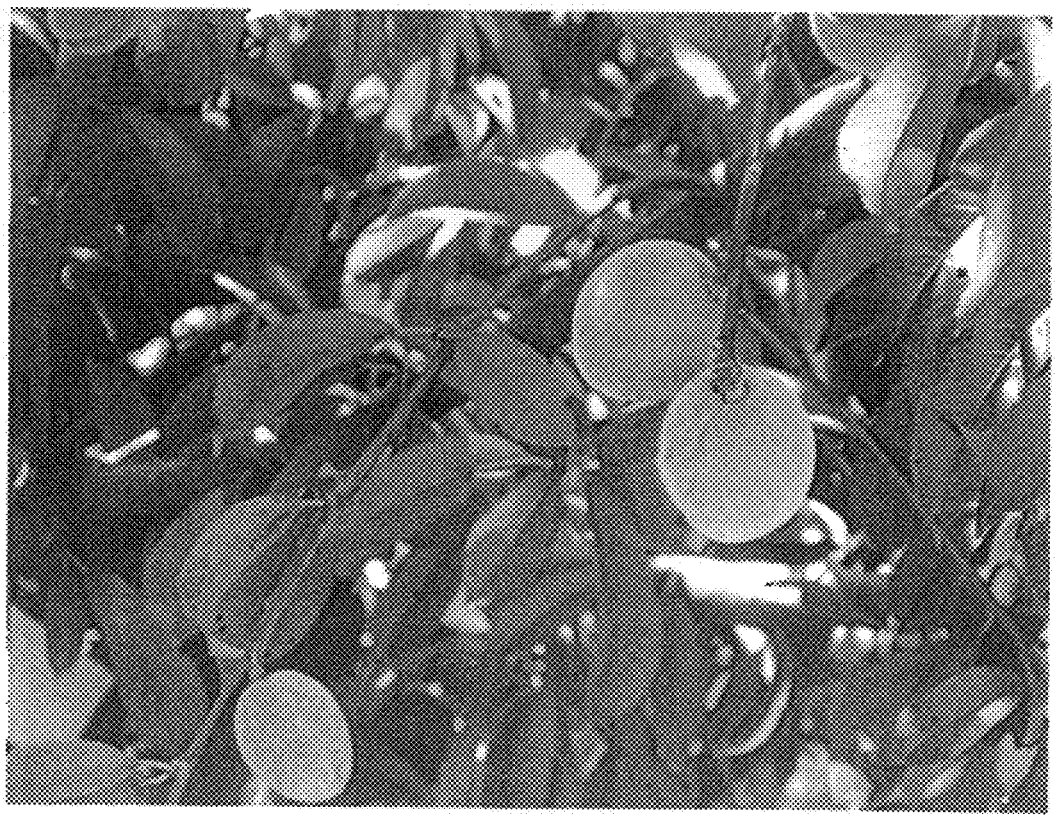
FIG. 3 depicts the fruiting characteristics of the second generation tree of the new variety at full harvest maturity.
Figure 4:
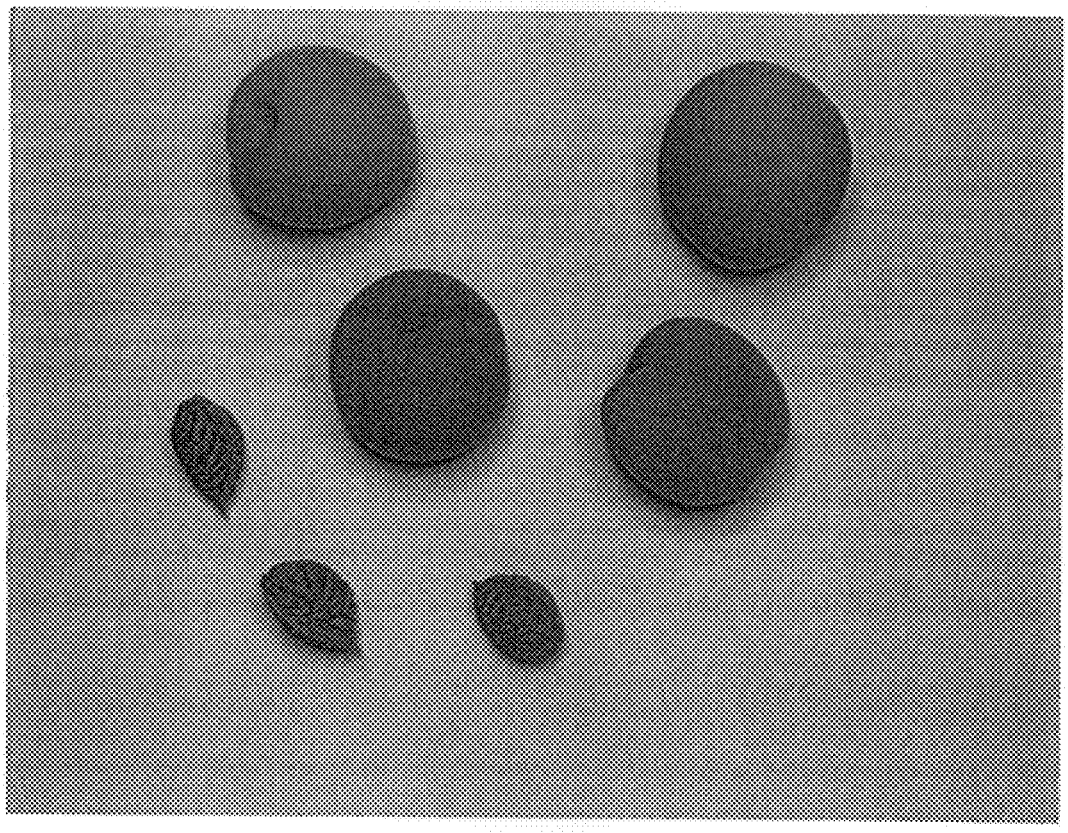
FIG. 4 shows the fruit of the present variety at harvest maturity and further shows several stones removed from the fruit.
Figure 5:
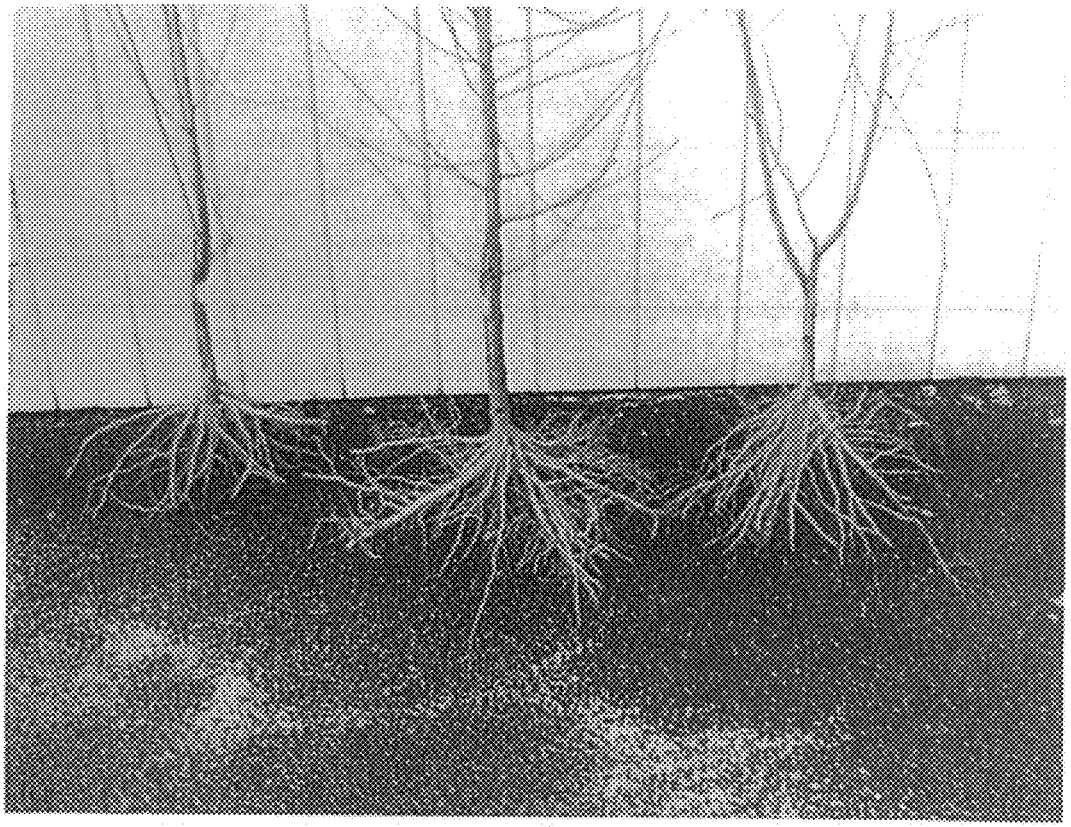
FIG. 5 depicts the root growth characteristics of the new variety of almond rootstock.

Tree form:

*Generally*.—Upright and spreading. The new variety of tree, which is seen in FIG. 1, was planted at the orchard of origin in the spring of 2009.

Tree productivity: Productive and producing small, greenish/yellow pubescent fruit which will be described, hereinafter.

Regularity of bearing: Considered regular; Hardiness: Considered hardy under typical Sacramento Valley climatic conditions.

Current growing conditions: The described trees are located in what is considered to be a high density planting. The distance between the rows is about 13.3 feet (4.1 meters). The trees are spaced at a distance of about 4 feet.

Tree width: When measured across the crown of the tree is approximately 10.5 feet within the row. The tree width as measured across the row measures about 12 feet.

Maximum tree height: About 15 feet when measured during the 2014 growing season.

Tree trunk thickness: About 15.2 centimeters when measured at a location approximately 3 centimeters above the graft union.

Trunk bark texture: Slightly roughened, and having a low, somewhat inconspicuous scarfskin.

Trunk bark lenticels:

*Numbers*.—Numerous.

Trunk bark lenticels:

*Appearance*.—Prominent and relatively large. The lenticels have a width of about 4 to about 9 millimeters; and further have a height of about 2 to about 3 millimeters.

Bark color: Considered medium gray (RHS 201B). Occasionally the bark appears a darker gray (RHS 201C).

Bark lenticel color: Dark gray along the margins (RHS 201B), and occasionally appearing RHS 201C.

Lenticel appearance:

*Generally*.—The centers of the lenticels are calloused and have a brown color (RHS 164B to 164A, respectively).

Winter hardiness and drought/heat tolerance: Presently unknown.

BRANCHES

Generally: As currently observed, the present trees have lowermost scaffold branches which fork from the trunk at a location which is about 25 centimeters above the graft union. The basal diameter of these two primary scaffolds branches measured about 10.2 centimeters, and 12.1 centimeters, respectively. Twelve (12) secondary branches arise from these two primary scaffolds.

Secondary branch diameters: About 2.8 to about 7 centimeters when measured at the branch base.

Upper vertical branches:

*Size*.—When measured at a distance of approximately 1.5 meters from the earth, these upper vertical branches have a thickness of about 1.9 centimeters to about 3.8 centimeters when measured at mid-shoot.

Smaller lateral branches:

*Size*.—These smaller, lateral branches arising from the vertical shoots, described above, range in thickness from about 0.3 centimeters to 0.8 centimeters when measured at their base.

Branch surface texture:

*Generally*.—The surface texture of the two scaffold branches and mature secondary branches is considered less rough than the bark texture of the trunk. Bark scarf skin is present, but is minimal in height.

Branch color: Gray, and ranging in color from RHS 197C to RHS 177B, respectively.

Branch lenticels:

*Size*.—Medium for the variety, and ranging in size from about 2 millimeters to about 6 millimeters in width; and about 1 millimeter to about 1.5 millimeters in height.

Lenticel color: Gray/brown, (RHS 197C), when seen along the perimeter, and brown, (RHS 165B), in the center of the lenticels where the interior, calloused region is present.

Internode length: Variable, about 2.6 centimeters to about 4.5 centimeters when measured on large, upright, secondary shoots. Smaller internode lengths are seen on smaller shoots, that is, those measuring about 1.3 centimeters, to about 3.3 centimeters.

Color of current shoots: The color as seen on mature and hardened shoots is brown, and somewhat variable between (RHS 199B to RHS 165B), and further having lighter brown striations (RHS 199B).

Color of immature shoots: Green (RHS 138C), and having areas of red when exposed to direct sunlight (RHS 47B to RHS 45D), respectively.

LEAVES

Leaf size: Generally considered average for the species.

Leaf length: Variable from about 9.8 to 13.6 centimeters, including the petiole.

Leaf width: About 3.2 to about 4.0 centimeters when measured at the widest point.

Leaf thickness:

*Generally*.—Considered average for the species.

Leaf form:

*Generally*.—Lanceolate. The leaves are often cupped or curved upwardly and inwardly.

Leaf tip form: Acuminate. The leaf apex is often twisted sideways.

Mature leaf color:

*Upper surface*.—Medium green (RHS 146A).

Mature leaf color:

*Lower surface*.—Green (RHS 138B).

Color:

*Shoot tips*.—On immature leaves this is considered lighter green in color. This color is not distinctive however.

Immature leaf:
*Top surface color*.—(RHS 146C);
*Immature leaves—bottom surface color*.—(RHS 138B).
Leaf margins:
*Generally*.—Crenate. The crenations are medium to large in size, and regular in shape.
Leaf marginal edge:
*Shape*.—Undulate.
Leaf petiole:
*Length*.—About 9 to about 12 millimeters in length, and about 1.5 to about 2 millimeters in thickness.
Leaf petiole:
*Color*.—Greenish yellow (RHS 145C). Petiole surfaces which are exposed to direct sunlight can have a reddish blush, (RHS 47B). Color variations within the petiole groove is minimal.
Leaf glands:
*Size*.—Considered relatively large, and having a reniform shape.
Leaf glands:
*Numbers*.—Two to 4 glands can be seen on the leaf blade, and are usually located, basally. Two to 5 additional glands can occur on a leaf petiole.
Leaf glands:
*Position*.—Alternate.
Leaf glands:
*Color*.—When new, the leaf glands are yellow-green in color (RHS 150A). The leaf glands darken with advancing senescence, and become somewhat deteriorated in the center.
Leaf stipules:
*Size*.—Variable from 8 to 9 millimeters in length, and when fully expanded.
Leaf stipules:
*Form*.—Linearly lanceolate.
Stipule margin:
*Shape*.—Coarsely serrate in form.
Stipule color: Light green/yellow when new (RHS 150A).
Leaf stipules:
*Form*.—Deciduous early after formation, and then the Stipules rapidly darken, deteriorate, and then fall off of the leaf.

FLOWERS

Bud size:
*Generally*.—Considered average for the species, and ranging from about 5 to 6 millimeters in length, and from 2 to 3 millimeters, in diameter, when measured at the bud base.
Bud form:
*Generally*.—Conic and considered relatively plump.
Bud site characteristics:
*Generally*.—The flower buds are relatively free from the stem surface, but are more appressed relative to the stem when only a single floral bud is present at the node.
Bud count per node:
*Generally*.—The bud count can range from 1 to 3. Frequently 2 to 3 floral buds are present.
Bud surface texture: The surface texture is highly pubescent, and has a gray, somewhat wooly, pubescence on the outer surface of the bud scale (RHS 201C to RHS 201D).
Bud color:
*Inner surface of the bud scale*.—Considered brown (RHS 175B), and having a glabrous surface texture.
Leaf buds:
*Size*.—Dormant leaf buds are of average size, having a length of about 3 to 4 millimeters, and a width of about 1.5 to 2.5 millimeters in diameter when measured at the bud base. The leaf buds are somewhat smaller than the flower buds.
Leaf bud form:
*Shape*.—Conic but thinner than the associated flower buds.
Leaf bud site characteristic: The leaf buds are moderately appressed relative to the bearing stem.
Leaf bud count per node: Typically 1 leaf bud is present per node.
Leaf bud surface character:
*Generally*.—The outer surface of the leaf buds are pubescent. The pubescence is gray in color (RHS 201C to about RHS 201D). The inner surface of the bud scale is generally glabrous, and has a brown color (RHS 175B).
Leaf bud hardiness: Considered hardy when grown under typical Sacramento Valley and San Joaquin Valley climatic conditions.
Date of first bloom: In 2013, this was observed on March 1.
Date of full bloom: Approximately 10 Mar. 2013 when observed at Newcastle, Calif. The full bloom occurs about 10 to 14 days later than the 'Nonpareil' and other almond varieties that are grown in the same vicinity, and is further approximately 4 days after the 'Mission' almond variety. The present variety blooms approximately 1 to 2 days earlier than the bloom date of peach tree varieties having approximately the same average chilling requirement as the present variety.
Flower size:
*Generally*.—Considered large and showy.
*Flower diameter*.—This dimension ranges from about 3.6 to 4.7 centimeters, when the flower is fully expanded.
Petal count:
*Generally*.—5.
Bloom quantity:
*Generally*.—Considered abundant.
Numbers of flowers: 1 to 4 flowers per node are typically observed. Usually 2 flowers are present.
Petal size:
*Length*.—About 1.4 to 2.2 centimeters, including the petal claw.
Petal width:
*Generally*.—About 1.1 centimeters to about 1.5 centimeters.
Petal claw:
*Form*.—Truncate.
Petal claw:
*Width*.—About 0.1 centimeters.
Petal claw:
*Length*.—About 0.15 centimeters to about 0.20 centimeters in length, and tapering basally.
Petal form: Ovate or occasionally considered weekly obovate. The petal has a slightly undulate petal margin and the individual petals are cupped in an inward direction.

Petal color:

*Young petals*.—Medium pink (RHS 65B). This color fades with advancing senescence to a lighter pink (RHS 69B).

Petal claw color: Generally speaking, the area immediately adjacent to the claw is a darker pink (RHS 65A).

Flower pedicel size: This is considered relatively short, and having a length of about 1 to 2 millimeters, and a thickness of about 1 millimeter.

Pedicel color: Shiny green (RHS 149B).

Pedicel surface texture:

*Generally*.—Considered glabrous. A basal ring is observed at the base of pedicel.

Calyx:

*Surface texture*.—Broadly wrinkled, and somewhat grooved, but considered substantially glabrous.

Calyx diameter: About 6 millimeters.

Calyx color: Yellow, basally (RHS 150B). The upper surface of the Calyx Cup is spotted and has a reddish/purple coloration, which is considered variable, from about RHS 181A to RHS 181B.

Sepals:

*Numbers*.—5.

Sepals:

*Form*.—Conic.

Sepal surface texture:

*Upper and lower surfaces*.—Glabrous.

Sepal margins: Considered highly pubescent, and having moderately long, wooly hairs.

Sepal pubescence:

*Color*.—Gray/white (RHS 156D).

Sepal size:

*Generally*.—The sepals range in length from about 5 to about 6 millimeters when fully expanded.

Sepal width: About 2.5 to about 3.5 millimeters when measured basally.

Sepal color: Reddish/purple, and which is variable, (RHS 181C to about RHS 181B). This is positioned over a greenish ground color (RHS 150B).

Floral nectarines:

*Color*.—Light orange, (RHS 162A) when young, and darkening, when advancing senescence, to RHS 22A, when viewed on more mature flowers.

Anther size:

*Length*.—About 0.15 centimeters.

Anthers:

*Width*.—About 0.10 centimeters. The anthers are considered plump and not shriveled.

Anther color:

*Dorsal surface*.—Red, (RHS 39A).

Anthers:

*Ventral surface*.—Yellow, (RHS 14D).

Filaments:

*Length*.—Considered variable from about 7 millimeters to about 12 millimeters.

Filament color: When the flower is immature, it is considered nearly white in color, and may have a light pink coloration (RHS 65D). When fully mature, the filaments are a dark violet color (RHS 61B). From the date of immaturity through to a fully mature flower, the stamens transition through many intermediate shades of color purple.

Pollen:

*Quantity*.—Abundant.

Pollen color: Yellow/gold (RHS 20A).

Pistil:

*Length*.—Variable from about 10 millimeters to about 18 millimeters including the ovary.

Pistil thickness: Variable, and measuring about 0.5 millimeters, in width, when measured at the center point.

Pistil color: Light green (RHS 1B).

Stigma:

*Color*.—A light/yellow/orange, (RHS 15D).

Pistil:

*Surface texture*.—Relatively glabrous when the upper half is considered. The lower half of the pistil is considered very pubescent.

Ovary:

*Length*.—About 3 to 4 millimeters.

Ovary:

*Width*.—About 1 to 2 millimeters.

Ovary:

*Surface texture*.—Highly pubescent, and having white/gray colored fibers (RHS 196D).

Ovary:

*Color*.—Typically the ovary is yellow/green in color (RHS 145C).

FRUIT

Generally: The current observations of the fruit were made on Aug. 13, 2013, at Newcastle, Calif. All the color code designation are made by reference to The Royal Horticulture Society London Colour Chart, Third Edition (1995).

Fruit maturity: Generally the present variety is ripe for harvesting approximately August 11 through Aug. 15, 2013, under the ecological conditions prevailing in Newcastle, Calif.

Fruit size:

*Generally*.—Considered small and uniform.

Fruit cheek:

*Diameter*.—About 3.8 cm to about 4.1 cm.

Fruit suture diameter:

*Generally*.—About 3.8 cm to about 4.2 cm.

Fruit axial length: About 3.3 cm to about 4.4 cm.

Fruit form:

*Generally*.—Considered globose to very slightly ovate when considered in its lateral aspect, and is further considered oval to very nearly globose when viewed from its apical aspect.

Fruit symmetry:

*Generally*.—Somewhat fully symmetrical, and occasionally slightly asymmetrical, and with one-half of the fruit being slightly larger than the other.

Fruit suture:

*Generally*.—Visible and extending from the base to the apex. The fruit suture appears deeper at, and across, the fruit apex, and within the fruit basin. No stitching or callous formation is visible on the suture, and no color is specifically associated with the suture.

Ventral surface of the fruit:

*Surface texture*.—This region can be occasionally considered quite smooth, but most often the fruit displays a very slightly lipped appearance. The aforementioned lipping, when present on the ventral surface, is more pronounced over the basal and apical shoulder areas.

Fruit stem cavity:

*Size*.—Considered small, and having a width of about 10 to 12 mm, and a length of about 13 to about 15 mm.

Fruit stem cavity:

*Shape*.—Oval in form.

Fruit stem cavity:

*Depth*.—About 8 to 9 mm. There is no specific coloration association with the stem cavity area.

Fruit base:

*Shape*.—Slight truncate. The fruit base is frequently at a right angle to the overall fruit axis.

Fruit apex:

*Form*.—Somewhat variable, but most frequently it will appear with a very short tip. However, and occasionally the fruit apex may appear depressed.

Fruit pistil point:

*Orientation*.—Considered oblique to the fruit axis. However, and occasionally the pistil point can be fully apical.

Fruit stem:

*Length*.—Considered short for the species, and having a length of about 3.5 to about 5.0 mm.

Fruit stem:

*Thickness*.—About 2 to about 2.5 mm.

Stem color: Yellow-green (RHS 145B) and having occasional areas of brown, (RHS 175A).

Fruit skin:

*Thickness*.—Considered relatively thick for the species.

Fruit skin:

*Surface texture*.—A short grayish-colored pubescence is present (RHS 196D).

Fruit skin:

*Flavor*.—Neutral to occasionally acidic in flavor.

Fruit skin:

*Attachment*.—Considered strong, until the underlying fruit is in a soft-ripe condition. When the fruit reaches a soft-ripe maturity the skin peels easily from the flesh.

Fruit skin:

*Tendency to split*.—The skin shows no tendency to crack or split.

Fruit skin:

*Coloration*.—Generally — At full maturity, most fruit are approximately 50% green, and yellow, but much variability in color can be present. The green color is (RHS 145C), and the yellow color is a pale yellow (RHS 160B). Occasionally some relatively thin red-colored striping can be present on the skin surface (RHS 39B). When red coloration does occur it usually covers only from about 3% to about 5% of the fruit surface.

Flesh color:

*Generally*.—Cream-yellow (RHS 11B), and occasionally a more greenish yellow (RHS 145B to 145C) respectively, may appear. The color of the flesh surrounding the stone is approximately similar to the overall flesh coloration.

Flesh texture:

*Generally*.—At harvest maturity, the flesh texture is soft and moderately fibrous.

Fruit ripening: The fruit appears to ripen first along the top of the basal shoulders.

Fruit aroma:

*Generally*.—Mildly aromatic, and having a pleasant aroma.

Fruit flavor:

*Generally*.—The fruit has poor eating quality. The flavor is acidic with moderate to strong astringency.

STONE

The stone is a clingstone which has many flesh fibers attached to the stone surface, throughout.

Stone size:

*Generally*.—Considered small for the species.

Stone length: About 2.4 to 2.8 cm.

Stone width: About 1.5 to about 1.6 cm.

Stone thickness: About 1.4 to 1.6 cm.

Fibers:

*Generally*.—Numerous relatively long fibers are present, and are attached to the stone surface in a multitude of places.

Stone form:

*Generally*.—Considered slightly variable, and most frequently oval. However and occasionally, stones may be found which tend to be slightly ovate in shape.

Stone base:

*Shape*.—Rounded and only occasionally truncate.

Stone hilum:

*Size*.—Small, and generally oval in form. The hilum is typically substantially eroded.

Stone apex:

*Generally*.—Pointed and having a sharp, dentate tip.

Stone size:

*Generally*.—The sides are usually equal and only occasionally slightly unequal sides are found on some stones.

Stone surface texture: Lateral surfaces of the stone have both pits and grooves present. As a general matter, the sides are more strongly grooved, and ridged near the stone edges. Still further, the lateral grooves are deep, coarse and ridged, throughout.

Ventral edge:

*Size*.—The ventral edge ranges in width from about 3 to about 4 mm when measured at mid-suture. The ventral edge wings are relatively low, and converge both basally, and apically.

Dorsal edge:

*Shape*.—The dorsal edge is subtended by a dorsal groove that is typically continuous from the stone tip, to the stone base. The dorsal groove can be transected in several places by deep, coarse, lateral grooves.

Stone color: The dry stone is a medium light brown (RHS 177C). The stone's color is substantially consistent throughout.

Tendency to split:

*Generally*.—There is no observed tendency for the stone to split.

Stone seed:

*Size*.—Relatively small. The stone seed has a length of about 13 mm to about 14.5 mm; a width of about 8 to about 9 mm; and a seed thickness of about 5-6 mm.

Seed form:

*Shape*.—Considered ovate. The embryo is plump and well filled.

Seed coat:

*Color*.—Light brown (RHS 165B), and further having some darker brown longitudinal striping (RHS 166C).

Resistance to root—knot nematode:

*Generally*.—The variety appears to be highly resistant or tolerant of Root-Knot nematode when grown under the ecological conditions prevailing in northern California.

Resistance to oak root fungus: The present variety seems to be highly resistant to this particular fungus.

Usage: The present variety is considered to be an ideal root stock for almonds and other similar varieties of trees.

Although the new variety of root stock possesses the described characteristics when grown under the ecological conditions prevailing in northern California, it should be understood that variations of the usual magnitude, and characteristics incident to changes in growing conditions; fertilization; pruning; pest control; frost; climatic variables; and horticultural management would be expected.

Having thus described and illustrated my new variety of root stock what I claim is new and desired is secured by Plant Letter Patent is:

1. A new and distinct variety of root stock substantially as illustrated and described and which is characterized principally as to novelty by its significant resistance to Oak Root fungus and Root-Knot nematode when compared to other common cultivars.

* * * * *